United States Patent [19]
Prince

[11] 3,950,554
[45] Apr. 13, 1976

[54] TREATMENT OF MASTITIS IN BOVINE UDDERS

[75] Inventor: Emanuel C. Prince, Jacksonville, Fla.

[73] Assignee: Southeastern Laboratories, Inc., Jacksonville, Fla.

[22] Filed: Jan. 31, 1974

[21] Appl. No.: 438,365

Related U.S. Application Data

[63] Continuation of Ser. No. 234,341, March 13, 1972, abandoned.

[52] U.S. Cl. ................ 424/273; 424/149; 424/150; 424/312; 424/326; 424/342; 424/346
[51] Int. Cl.² ................ A61K 31/23; A61K 31/415
[58] Field of Search .......... 424/365, 312, 149, 150, 424/273, 326, 342, 346

[56] References Cited
UNITED STATES PATENTS

3,222,252   12/1965   Kraus.................................. 424/312

OTHER PUBLICATIONS

Keeping Livestock Healthy, (1942), U.S. Department Agriculture, pp. 519–521.

*Primary Examiner*—Sam Rosen
*Attorney, Agent, or Firm*—Fisher, Christen & Sabol

[57] ABSTRACT

Mastitis in bovine udders is treated and controlled by dipping the teats into a composition consisting essentially of a semi-drying oil and a fatty acid ester and allowing the teat to dry to form a water repellent film on the teat skin and across the teat orifice. The composition may also contain a bactericide, a healing agent, a hydration agent and a dye.

10 Claims, No Drawings

TREATMENT OF MASTITIS IN BOVINE UDDERS

This is a continuation of application Ser. No. 234,341 filed Mar. 13, 1972 and now abandoned.

The present invention relates to the treatment of disease in bovine udders. More particularly, the present invention relates to a composition and method for the prevention and treatment of mastitis.

Mastitis is a highly infectious disease which afflicts the bovine udder. The losses in dairy production resulting from the prevalence of this disease are staggering. For example, in the United States alone, these losses are estimated to be in the hundreds of millions of dollars. Mastitis not only reduces the production of higher yielding animals, but also shortens their productive life.

It is well known that mastitis is transmitted from animal to animal. It has also been established that the only route of transmission of the disease is through the teat orifice. Conditions which are held primarily responsible for the high incidence of mastitis include poor udder hygiene and physical damage to the teats. Dairymen and veterinarians have long sought a conditioning and protective composition which is economical and also provides facility of use. A composition which would improve the normal condition of the udder and teats and would also aid in preventing or effectively reducing the incidence of mastitis would serve to substantially increase both the production and productive life of a dairy herd.

Infectious mastitis is caused by microorganisms and many prior art treatments have been only partially effective in controlling the disease. For example, compounds such as sulphanilimide are useful against one type of microorganism which causes mastitis but are not useful against other types. Since the infection is usually of a mixed character, it follows that the effectiveness of sulphanilimide is limited for all practical purposes. It has also been suggested to use penicillin for the treatment of mastitis. However, the high cost and extraordinary conditions necessary for the preservation and use of penicillin result in its being of minimal practical value.

It has been proposed in U.S. Pat. No. 3,222,252 to treat mastitis with a preparation which comprises a blend of edible semi-drying oils and drying oils together with a fatty acid ester skin emollient film forming agent. It is taught in this patent that the presence of a drying oil in the preparation is essential to provide the desired film forming property.

It is an object of the present invention to provide a composition and method for the treatment of mastitis in bovine udders.

It is another object of the present invention to provide such a composition and method which overcomes the shortcomings of treatments of the prior art.

It is a further object of the present invention to provide such a composition which is economical and easily applied for the effective prevention, treatment and control of mastitis.

It is still another object of the present invention to provide such a composition which is non-toxic and which may be used frequently over long periods of time within adversely affecting udder tissue.

Still further objects and the entire scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from this detailed description.

It has been found that the above objects may be attained by a composition which contains as essential ingredients an edible semi-drying oil or mixture of semi-drying oils and a fatty acid ester. As will be more fully explained hereinafter, the composition may also contain additives for various purposes. The composition may be applied in any suitable manner. Preferably application is by dipping the teat into the composition and allowing the teat to dry. Also preferably the composition is used twice daily, i.e. after each milking.

Suitable semi-drying oils for use in the composition of the present invention include soybean oil, cotton seed oil, sesame oil, beechnut oil, corn oil and mixtures thereof. Preferred semi-drying oils include soybean oil and cotton seed oil. The above oils are non-toxic, substantially tasteless and odorless vegetable oils and the drying characteristics thereof are due partially to the degree of unsaturation and the structure of the component glycerides.

Suitable fatty acid esters for use in the present invention include all fatty acid esters of low molecular weight monohydric alcohols, such as butyl stearate, isopropyl palmitate, isopropyl myristate, etc., and these esters are preferred. A particularly preferred ester is the combination of palmitate and myristate which is commercially available under the trademark Deltyl Extra and consists of isopropyl palmitate-myristate. Also suitable are all polyol esters of fatty acids such as glycerol monostearate, propylene glycol monostearate, ethylene glycol monostearate and polyethylene glycol monostearate. The fatty acid esters serve as skin emollients and also aid in formation of a non-tacky film when the composition of the present invention is dried after use.

For purposes of the present invention, the semi-drying oil component is present from about 86% to about 98% by weight, preferably from about 90% to 98% by weight, and the fatty acid ester component is included in a proportion of up to about 10% by weight, e.g. from about 2% to about 10% by weight, preferably from about 5% to 8% by weight.

Other ingredients or additives which are beneficially included in the composition of the present invention include a bactericidal or bacteristatic agent such as tamed iodine, hexachlorophene, phenol, etc., a healing agent such as allantoin and a hydration agent such as cetyle alcohol. The composition may also optionally contain a coloring agent or edible dye such as carotene.

The bactericidal agent is used for its disinfectant properties and may be soluble or dispersable as a suspension in the oleaginous base of the composition. One preferred bactericidal agent is tamed iodine or iodophor. These terms are applied to products wherein surface active agents (such as nonoxynol or Monosan-IOD) act as carriers and solubilizing agents for iodine. An iodophor enhances the bactericidal activity of iodine while reducing the vapor pressure and odor. Staining is virtually non-existent both to skin and natural fabrics and wide aqueous dilution is possible. Preparation of iodophor is disclosed, for example, in U.S. Pat. Nos. 2,710,277 and 2,977,315.

Iodophor is particularly desirable for purposes of the present invention since it is virtually non-stinging and is also film-forming. It is a topical antiseptic that essentially retains the nonselective broad-range microbial activity of iodine, yet without the undesirable features inherent in iodine tincture and Lugol's solution, being nonirritating to skin and mucous membranes. Iodophor products kill bacteria (including antibiotic resistant organisms), fungi, viruses, protozoa and yeasts, and have a more prolonged germicidal action than ordinary iodine solutions, maintaining microbial action in the presence of blood, serum pus or necrotic tissue.

Tamed iodine is available commercially in several forms including the iodophor and solutions of varying concentrations. While not restricted to the same, the iodophor as such is preferably used in the present invention and may be used in amounts up to about 2.0% by weight, e.g. from 0.1% to 1.0% by weight. Preferably the iodofor is used in amounts to provide from about 50 to about 100 ppm., e.g. about 75 ppm., available iodine in the final composition. Solutions of varying concentrations may be used in corresponding amounts.

Other preferred bactericides include chlorhexidine or one of its salts such as the diacetate, cresol, paraformaldehyde, sodium hyprochlorite and a sodium hypochlorite solution containing about 5 ppm. free chlorine. These bactericides may be used in amounts up to about 2.5% by weight of the compositions of the present invention, e.g. from about 0.1% to about 1.0% by weight.

Both chlorhexidine and its diacetate are topical antiseptics. The chlorhexidine may be used as a suspension in, for example, glycerol, a glyceride, ehtylene glycol or propylene glycol. The diacetate is soluble in these compounds. Cresol is available commercially and is a mixture of ortho-meta- and paracresol. The paraformaldehyde and sodium hypochlorite may also be used in the form of a suspension.

When hexachlorophene is used as the bactericidal agent, it may be included in amounts up to about 2.0% by weight. e.g. from about 0.1% to about 1.0% by weight. When phenol is used as the bactericidal agent, it is included in amounts up to about 0.67% by weight, e.g. from about 0.125% to 0.67% by weight.

For purposes of the present invention, the bactericidal agent is said to be used in an effective amount, i.e. an amount which, in the final composition, will kill or substantially reduce the number of bacteria normally found on the bovine udder and especially those which tend to cause or aggravate mastitis. Specific amounts will vary depending upon the bactericidal agent included and on the comparative strength or concentration of the form of the agent used. Generally speaking, effective amounts will fall within the ranges of up to 2.5% by weight, e.g. from 0.1 to 1.0% by weight, of the final composition.

The healing agent is used both for its curative action and for stimulation of formation of new tissue. Allantoin is the preferred healing agent and may be used in amounts up to 0.1% by weight, e.g. from about 0.01 to 0.1% by weight. While not soluble in the oleaginous base of the composition, the allantoin is distributed therein in the form of a fine suspension obtained by vigorous mixing.

The hydration agent is used to induce hydration of dry tissue and to aid in formation of water repellent surface film. The preferred hydration agent is cetyl alcohol, although other related alcohols such as stearyl alcohol, lauryl alcohol and myristyl alcohol may be used. The hydration agent may be used in amounts up to about 2.0% by weight, e.g. from about 0.1% to 2.0% by weight.

As earlier indicated, the composition of the present invention may be applied to the bovine udder by any suitable method. Preferably application is by dipping the teat into the composition immediately after milking and allowing the teat to dry. Regularly scheduled use of the composition of the present invention results in stability or reduction of bacteria counts and in improved skin tone with absence of chapping or roughening of the skin of the teat. Smooth skin is easier to maintain clean and harbors less bacteria than roughened and chapped teats. Each individual application of the composition provides, upon drying, a protective water repellent film over the teat tissue and across the teat orifice.

The composition of the present invention may thus include ingredients in the operable and preferred amounts shown in Table I.

Table I

| Ingredient | Operable | Percent by weight Preferred |
|---|---|---|
| Semi-drying oil | 86–98 | 90–98 |
| Fatty acid ester | 2–10 | 5–8 |
| Bactericide | 0–2.5 | 0.1–1.0 |
| Healing agent | 0–0.1 | 0.01–0.1 |
| Hydration agent | 0–2.0 | 0.1–2.0 |
| Dye | 0–Trace | Trace |

The compositions are prepared by mixing the ingredients to obtain a homogeneous product. In one embodiment, any additives used may be premixed with the fatty acid ester and later mixed with the semi-drying oil, e.g. at time of use. Optionally, to aid in ease and speed of mixing, solid ingredients, e.g. phenol, may be separately melted before addition to the composition or any part thereof.

The following specific examples are to be considered only as illustrative of preferred embodiments of the present invention.

Example 1

| Ingredient | Amount (pounds) | % by weight |
|---|---|---|
| Soybean oil | 1389 | 92.60 |
| Isopropyl myristate | 69 | 6.60 |
| Isopropyl palmitate | 30 | |
| Cetyl alcohol | 2 | 0.13 |
| Phenol, U. S. P. | 10 | 0.67 |

The isopropyl myristate and isopropyl palmitate were mixed in a 220 gallon capacity stainless steel tank and warmed to 55°C. with an electric immersion heater, and the cetyl alcohol was added with stirring. The phenol was separately melted by warming to 50°C. on a hot plate and then added to the isopropyl myristate-isopropyl palmitate-cetyl alcohol solution and stirred until the mixture was completely homogeneous. The soybean oil was then added with continued stirring to form a final homogeneous product which was then packaged in 1 and 5 gallon tin-lined containers.

Example 2

| Ingredient | Amount |
| --- | --- |
| Soybean oil | 1389 pounds |
| Isopropyl myristate | 69 pounds |
| Isopropyl palmitate | 30 pounds |
| Tamed iodine | 13 pounds |

The procedure of Example 1 was repeated with the exception that the tamed iodine was added to the isopropyl myristate-isopropyl palmitate-cetyl alcohol solution with stirring to form a homoegenous mixture. The tamed iodine was provided 75 ppm. available iodine in the final composition.

Example 3

| Ingredient | % by weight |
| --- | --- |
| Soybean oil | 90.6 |
| Isopropyl palmitate-myristate (Deltyl Estra) | 6.8 |
| Hexachlorophene | 2.0 |
| Cetyl alcohol | 0.5 |
| Allantoin | 0.1 |
| Carotene | |

The isopropyl palmitate-myristate was heated to about 80°C. and the cetyl alcohol was dissolved therein. The resulting solution was blended with the remaining ingredients and stirred to form a homogeneous mixture.

EXAMPLE 4

Example 3 was repeated using 0.5% by weight chlorhexidine as a suspension in glycerol in place of the hexachlorophene and increasing the amount of soybean oil to 92.1% by weight.

EXAMPLE 5

Example 3 was repeated using 0.5% by weight tamed iodine (providing 75 ppm. available iodine) in place of the hexachlorophene and adjusting the amount of soybean oil to 92.0% by weight.

The above examples illustrate the embodiment of the present invention wherein the complete composition is initially mixed together. The following examples illustrate the embodiment wherein the additives are premixed with the fatty acid ester to form a concentrate which may be mixed with the semi-drying oil at any time, for example at the time of use.

EXAMPLE 6

The following ingredients were combined with mixing to form a homogeneous mixture:

| Ingredient | Amount |
| --- | --- |
| Isopropyl palmitate-myristate | 7.7 pounds |
| Hexachlorophene | 21.4 ounces |
| Cetyl alcohol | 5.4 ounces |
| Allantoin | 0.18 ounces |

The mixture was combined with 69.3 pounds cotton seed oil. The final product had the following composition.

| Ingredient | % by weight |
| --- | --- |
| Cotton seed oil | 88.07 |
| Isopropyl palmitate-myristate | 9.79 |
| Hexachlorophene | 1.70 |
| Cetyl alcohol | 0.42 |
| Allantoin | 0.02 |

EXAMPLE 7

Example 6 was repeated using 0.5% by weight of paraformaldehyde as a suspension in place of the hexachlorophene and adjusting the amount of cotton seed oil to 89.27% by weight.

The following example illustrates a still further embodiment of the present invention.

Example 9

| Ingredient | Amount (pounds) | % by weight |
| --- | --- | --- |
| Soybean oil | 1389 | 92.60 |
| Isopropyl palmitate-myristate | 99 | 6.60 |
| Cetyl alcohol | 2 | 0.13 |
| Chlorhexidine diacetate | 10 | 0.67 |

The isopropyl palmitate-myristate was heated to 55°C. and the cetyl alcohol was dissolved therein with stirring. The chlorohexidine diacetate was dissolved in a small amount propylene glycol and added to the isopropyl palmitate-myristate-cetyl alcohol solution and stirred until the mixture was completely homogeneous. The soybean oil was then added with continued stirring to form a final homogeneous product.

What is claimed is:

1. A composition for the treatment of mastitis in udders which consists of an effective amount of an edible semi-drying oil and a fatty acid ester of an alcohol selected from the group consisting of low molecular weight monohydric alcohols, glycerol, propylene glycol, ethylene glycol and polyethylene glycol.

2. The composition according to claim 1 wherein the semi-drying oil is present in an amount of from about 90% to about 98% by weight and the fatty acid ester is present in an amount of from about 2% to about 10% by weight.

3. The composition according to claim 1 wherein the semi-drying oil is selected from the group consisting of soybean oil, sesame oil, cotton seed oil, beechnut oil, corn oil and mixtures thereof.

4. The composition according to claim 1 containing also an effective amount of a bactericidal agent.

5. The composition according to claim 4 wherein the bactericidal agent is included in an amount up to about 2.5% by weight.

6. The composition according to claim 4 wherein the bactericidal agent is included in an amount of from 0.1% to about 1.0% by weight.

7. A method for the treatment of mastitis in bovine udders which comprises applying to the udder teats the composition of claim 1 and allowing the teat to dry thereby forming a water repellent film on the teat skin and across the teat orifice.

8. The method according to claim 7 wherein the composition is applied by dipping the teat into said composition.

9. The composition according to claim 4 containing also a member selected from the group consisting of allantoin and a hydration agent selected from the group consisting of cetyl alcohol, stearyl alcohol, lauryl alcohol and myristyl alcohol and mixtures thereof.

10. The composition according to claim 9 wherein the allantoin is present in the amount of from about 0.1% to about 1.0% by weight and the hydration agent is present in an amount of from about 0.1% to about 2.0% by weight.

* * * * *